US006316667B2

(12) United States Patent
Giannessi et al.

(10) Patent No.: US 6,316,667 B2
(45) Date of Patent: Nov. 13, 2001

(54) PROCESS FOR THE PREPARATION OF R-(-)-CARNITINE

(75) Inventors: Fabio Giannessi, Pomezia; Maria Ornella Tinti; Francesco De Angelis, both of Rome, all of (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/740,806

(22) Filed: Dec. 21, 2000

Related U.S. Application Data

(63) Continuation of application No. PCT/IT99/00241, filed on Jul. 27, 1999.

(30) Foreign Application Priority Data

Jul. 31, 1998 (IT) ..... MI98A1796

(51) Int. Cl.[7] ..... C07C 229/00
(52) U.S. Cl. ..... 562/567; 562/553
(58) Field of Search ..... 562/567, 553

(56) References Cited

U.S. PATENT DOCUMENTS 5,473,104 12/1995 McCarthy .
5,599,978 * 2/1997 Giannessi et al. .

FOREIGN PATENT DOCUMENTS 0 609 643 A 8/1994 (EP) .

OTHER PUBLICATIONS

Patent Abstracts of Japan vol. 016, No. 431 (C–0983), Sep. 1992, & JP 04 149151 A (Kanegafuchi Chem Ind Co Ltd), May 1992.

M. Larcheveque et al.: "Enantiomerically pure beta, gamma–epoxaesters from beta–hydroxylactones: synthesis of beta–hydroxyesters and (–)–GABOB" Tetrahedron., vol. 46, No. 12, 1990, Elsevier Science Publishers, Amsterdam., NL.

T. Kaneko et al.: "On the absolute configuration of L–cartinine" Bulletin of the Chemical Society of Japan., vol. 35, 1962, pp. 1153–1155, Japan Publications Trading Co. Tokyo., JP.

* cited by examiner

*Primary Examiner*—Gary Geist
*Assistant Examiner*—Hector M Reyes
(74) *Attorney, Agent, or Firm*—Nixon & Vanderhye

(57) ABSTRACT

R-(–)-carnitine is prepared by (a) conversion of (S)-3-hydroxy-4-butyrolactone [1] to alkyl (S)-4-halogen-3-hydroxy-butyrate [2] by reaction with a linear or branched $C_1$–$C_7$ alcohol (b), substitution of a CN group for the halogen of compound [2] to yield the alkyl ester of (R)-4-cyano-3-hydroxybutyric acid [3], (c) conversion of alkyl ester [3] to yield (R)-4-cyano-3-hydroxybutyramide [4], (d) cyclization of compound [4] to yield (R)-5-(cyanomethyl)-2-oxazolidone [5] via conversion of the amide function to isocyanate, (e) hydrolysis of compound [5] to yield (R)-4-amino-3-hydroxybutyric acid [6], and finally (f) methylation of the amino group of compound [6] to yield the end product (R)-carnitine.

12 Claims, No Drawings

PROCESS FOR THE PREPARATION OF R-(-)-CARNITINE

This application is a continuation of Ser. No. PCT/IT 99/00241 filed Jul. 27, 1999.

The invention described herein relates to a chemical process for the stereoselective synthesis of R-(−)-carnitine.

As is known, carnitine contains an asymmetry centre and can therefore exist in the form of two enantiomorphs, designated R-(−)-carnitine and S-(+)-carnitine, respectively. Of these, only R-(−)-carnitine is present in living organisms where it acts as a carrier for the transport of fatty acids across the mitochondrial membranes. Whereas R-(−)-carnitine is the physiologically active enantiomorph, for some years the R,S racemate has been used as a therapeutic agent. It has had to be acknowledged, however, that S-(+)-carnitine is a competitive inhibitor of carnitine acetyltransferases and can lower the levels of R-(−)-carnitine in the myocardium and in skeletal muscle.

It is therefore essential that only R-(−)-carnitine be administered to patients undergoing haemodialysis treatment or those under treatment for cardiac or lipid metabolism disorders.

The same principle applies to the therapeutic use of derivatives of carnitine for the treatment of disorders of cerebral metabolism, peripheral neuropathies, peripheral arteriopathies, etc., for which acetyl R-(−)-carnitine and propionyl R-(−)-carnitine are used, obtained by acylation of R-(−)-carnitine.

Various chemical processes have been proposed for the production of carnitine on an industrial scale. These processes are generally non-stereospecific and therefore lead to racemic mixtures of R and S isomers. Consequently, resolution methods must be used to separate the constituent enantiomorphs of the racemate. Typically, the R,S racemic mixture is reacted with an optically active acid, selected, for example, from d-tartaric acid or d-camphorsulphonic acid, obtaining two diastereoisomers that can be separated from each other. In the classic process described in U.S. Pat. No. 4,254,053, d-camphoric acid is used as the resolvent of a racemic mixture of R,S carnitinamide, obtaining S-(+)-carnitinamide as the waste product, while the R-(−)-carnitinamide is hydrolysed to R-(−)-carnitine.

These resolution processes are therefore complex and expensive and, in any case, lead to the production of both R-(−)-carnitine and an equal amount of S-(+)-carnitine or of a precursor with, however, the opposite configuration to that of R-(−)-carnitine, as a by-product.

In an attempt to use the substantial amounts of S-(+)-carnitine (or of a precursor, such as S-(+)-carnitinamide) which are obtained as a waste product in the industrial production of R-(−)-carnitine, various microbiological processes have recently been proposed based on the stereospecific synthesis of R-(−)-carnitine starting from achiral derivatives (crotonobetaine or gamma-butyrobetaine) obtained precisely from this S-(+)-carnitine waste product.

These processes are generally based on the stereospecific hydration of crotonobetaine and differ from one another mainly in the particular micro-organism used to produce the biotransformation. See, for example, the processes described in: EP 0121444 (Hamari), EP 0122794 (Ajinomoto), EP 0148132 (Sigma-Tau), JP 275689/87 (Bioru), JP 61067494 (Seitetsu), JP 61234794 (Seitetsu), JP 61234788 (Seitetsu), JP 61271996 (Seitetsu), JP 61271995 (Seitetsu), EP 0410430 (Lonza), EP 0195944 (Lonza), EP 0158194 (Lonza), EP 0457735 (Sigma-Tau).

JP 62044189 (Seitetsu) describes a process for the stereoselective production of R-(−)-carnitine, starting, instead, from gamma-butyrobetaine, which in turn is obtained from crotonobetaine by an enzymatic method.

All these processes present drawbacks and pose major technical problems.

In the first place, S-(+)-carnitine has to be converted to the achiral compound (crotonobetaine or gamma-butyrobetaine) which constitutes the starting product in all the aforementioned microbiological processes.

The latter present one or more of the following problems in production on an industrial scale:

(i) the R-(−)-carnitine yield is extremely low;

(ii) the micro-organisms must be grown on expensive nutrient media;

(iii) the micro-organisms support only low concentrations of crotonobetaine (up to 2–3% (w/v));

(iv) side reactions occur, such as, in the case of the use of crotonobetaine, for instance, the reduction of the latter to gamma-butyrobetaine, or the oxidation of R-(−)-carnitine to 3-dehydrocarnitine, which diminish the final R-(−)-carnitine yield.

More recently, a chemical process has been described (U.S. Pat. No. 5412113; U.S. Pat. No. 5599978; EP 0609643) based on the conversion to R-(−)-carnitine of a starting compound containing one asymmetric carbon atom with the opposite configuration to that of R-(−)-carnitine, without this compound having first to be converted to the achiral intermediate, crotonobetaine or gamma-butyrobetaine, and this achiral intermediate having to be later converted to R-(−)-carnitine. The starting compound consists in S-(+)-carnitinamide, which, as mentioned above, is obtained as a redundant waste product in the resolution of the R,S-carnitinamide racemic mixture by means of, for instance, d-camphoric acid. According to this process, the S-(+)-carnitinamide is converted to S-(+)-carnitine; the latter is esterified to protect the carboxyl group; the ester is acylated, preferably mesylated; after restoring the carboxyl group, the acyl derivative thus obtained is converted to a chiral lactone presenting the desired R configuration, which, through basic hydrolysis, supplies the R-(−)-carnitine.

It should be noted that both in the microbiological processes that obtain R-(−)-carnitine via an achiral intermediate and in the chemical process that enables R-(−)-carnitine to be obtained via chiral lactone, the starting product is a precursor of carnitine with the opposite configuration to that of the R form normally obtained by resolution of racemic mixtures, e.g. from R,S-carnitinamide.

The advantages to be gained from a process which makes it possible to start from a precursor which is not necessarily related to the prior resolution of racemic mixtures of R,S-carnitine, but which can also be obtained from alternative sources, appear clear.

A process for the preparation of (R)-carnitine starting from (S)-3-hydroxy-4-butyrolactone has now been found and constitutes part of the invention described herein.

(S)-3-hydroxy-4-butyrolactone can be obtained in industrial quantities by conversion of D-hexoses, particularly D-glucose (EP 0513 430), or, alternatively, can be obtained by transforming the S-carnitine isomer, a waste product of the industrial synthesis of R-carnitine, as described in Giannessi F., De Angelis F. RM95A000652; Calvisi G., Catini R., Chiarotti W., Giannessi F., Muck S., Tinti M. O., De Angelis F. *SYNLETT* 1997, 71–74.

The process according to the invention is represented by the following reaction diagram:

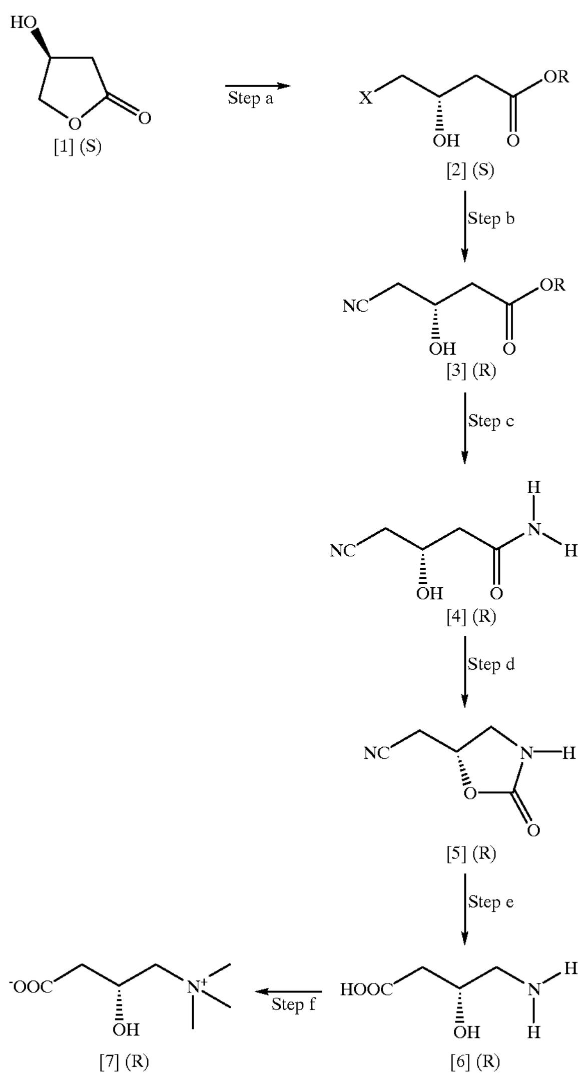

where X is halogen and R a linear or branched $C_1$–$C_7$ alkyl.

In step a, (S)-3-hydroxy-4-butyrolactone [1] is converted to alkyl (S)-4-halogen-3-hydroxybutyrate [2] by reaction with a linear or branched $C_1$–$C_7$ alcohol; the alcohol shall preferably be selected from the group consisting of methanol, ethanol, isopropanol and isobutanol.

The conversion can be done by means of known techniques, for example, as described in (Larcheveque M., Henrot S., *Tetrahedron*, 1990, 46, 4277–4282), where the synthesis of the ethyl ester of 4-iodo-3-hydroxybutyric acid is described, and in (Toaka N., Kamiyama N., Inoue K., Takahashi S. (Kanegafuchi) JP 04149151, 1992; *Chem. Abstr*. 1992, 117, 191350p, where the synthesis of the methyl ester of 4-bromo-3-hydroxybutyric acid is reported.

The preferred process is the one described in *Tetrahedron*, 15 1990, 46, 4277–4282, in which isobutanol is used.

In step b, a CN group is substituted for the halogen present in compound [2] to yield the alkyl ester of (R)-4-cyano-3-hydroxybutyric acid [3]. This substitution, of the nucleophilic type, can be done by solubilising compound [2] in an organic solvent selected from the group consisting of dimethylformamide (DMF), dimethylsulfoxide (DMSO), acetonitrile ($CH_3CN$) or mixtures of these with $H_2O$, in a ratio from 10:1 to 1:10, preferably in mixtures of $CH_3CN/H_2O$ in a ratio from 2:1 to 6:1, and most preferably 5:1, and reacting compound [2] with KCN in a KCN:compound [2] ratio ranging from 1:1 to 6:1, preferably 3:1 to 5:1, and even more preferably 4:1, for a time period ranging from 1 to 12 hours, preferably 1 to 2 hours, and even more preferably 1.25 hours, at temperatures ranging from ambient temperature to the boiling point of the solvent or mixture, preferably from 60 to 90° C., and even more preferably 80° C.

In step c, the ester function of compound [3] is converted to an amide function to yield (R)-4-cyano-3-hydroxybutyramide [4]. This conversion can be accomplished by dissolving compound [3] in a solvent selected from the group consisting of methanol (MeOH), ethanol (EtOH), isopropanol (iPrOH), preferably MeOH, and saturating the solution with gaseous $NH_3$ and cooling in an ice bath. The solution thus obtained is left at temperatures ranging from ambient temperature to 60° C., preferably at ambient temperature, for time periods ranging from 8 to 72 hours, preferably from 24 to 60 hours, and even more preferably for 48 hours, repeating the ammonia insufflation operation 3 to 5 times in the course of the reaction, preferably 4 to 5 times, for 10 to 20 minutes each time, and even more preferably 4 times, each of 15 minutes' duration.

Steps b and c can be done in sequence without purifying the product obtained from step b.

In step d, compound [4] is cyclised to yield (R)-5-(cyanomethyl)-2-oxazolidone [5] via transformation of the amide function to isocyanate.

The transformation to isocyanate, with consequent cyclisation due to the presence of the hydroxyl in β, can be done by means of known techniques (Hofmann rearrangement). In particular, compound [4], after solubilisation in an organic solvent selected from the group consisting of $CH_3CN$, DMF, DMSO and mixtures of these with $H_2O$ in solvent:$H_2O$ ratios ranging from 10:1 to 1:10, preferably in a mixture of $CH_3CN$ and $H_2O$ in ratios from 1:2 to 2:1, and even more preferably in a 1:1 ratio, is reacted with bis [trifluoroacetoxy]phenyl iodide (PIFA) with compound [4]:PIFA ratios ranging from 1:1 to 6:1, preferably from 1:1 to 3:1, and even more preferably in a ratio of 1.5:1, in the presence or absence of an organic base comprising a tertiary amine, preferably selected from among the group consisting of pyridine, triethylamine, trimethylamine, picoline and lutidine, added with a compound [4]:base ratio from 1:1 to 1:3.

In step e, compound [5] is hydrolysed to yield (R)-4-amino-3-hydroxybutyric acid [6] ((R)-GABOB).

The hydrolysis can be done with an aqueous solution of a strong acid, preferably HCl at a concentration ranging from 1N to 12 N, preferably from 2N to 6N, for time periods ranging from 1 hour to 7 days, preferably from 3 hours to 6 days, at temperatures ranging from ambient temperature to the reflux temperature of the acid solution, preferably from 80° C. to the reflux temperature of the solution. The-preferred conditions for the hydrolysis axe HCl 3N for 5 days at 100° C. or HCl 6N for 6 hours at the reflux temperature.

In step f, the amino group of compound. [6] is trimethylated to yield the end product (R)-carnitine by means of known methods (Kaneko T., Yoshida R., *Bull. Chem. Soc. Jap*., 1962, 35. 1153).

The following example illustrates the invention in greater detail:

EXAMPLE

Preparation of isobutyl (S)-4-iodo-3-hydroxybutyrate [2] (Step a)

The process described in Tetrahedron 1990, 46(12), 4277–4282 was adopted, using isobutyl alcohol instead of ethyl alcohol starting from 10 g (S)-3-hydroxy-4-butyrolactone. 24 g of oily product were obtained; yield=85%; $^1$H NMR ($CDCl_3$, 300 MHz) δ 3.95 (m, 1H), 3.85 (d, 2H), 3.25 (m, 2H), 3.10 (d, 1H), 2.60 (m, 2H), 1.90 (m, 1H), 0.90 (d, 6H); $[\alpha]_D^{20}$=−12.2° (c=1, $CHCl_3$); C, H, N values calculated for $C_8H_{15}IO_3$: C, 33.58; H, 5.28; found: C, 33.91, H, 5.40.

Preparation of isobutyl (R)-4-cyano-3-hydroxybutyrate [3] (Step b)

To isobutyl (S)-4-iodo-3-hydroxybutyrate (5.72 g, 19.99 mol) was added KCN (5.26 g, 80.77 mol) and the solution was left to stir at 80° C. for 1.25 hours. The $CH_3CN$ was vacuum-evaporated, $H_2O$ (30 mL) was added to the residue, the solution was extracted with $Et_2O$ (3×100 mL), the organic phase was dried on anhydrous sodium sulphate, filtered and vacuum dried. 2.04 g of product (yield=55%) were obtained and used as such in the following reaction.

For analytical purposes, a sample was purified by flash chromatography on silica gel using hexane-EtOAc (ethyl acetate) as the eluent in a ratio of 75:25, yielding the product as an oil. $^1$H NMR ($CDCl_3$, 300 MHz) δ 4.38 (m, 1H), 3.95 (d, 2H), 3.50 (s, 1H), 2.65 (m, 4H), 1.95 (m, 1H), 0.95 (d, 6H); $[\alpha]_D^{20}$=+4.0° (c=0.96, $H_2O$); C, H, N values calculated for $C_9H_{15}NO_3$: C, 58.36; H, 8.16; N, 7.56; found: C, 57.85, H, 8.71; N, 7.30.

Preparation of (R)-4-cyano-3-hydroxybutyramide [4] (Step c)

In a solution of isobutyl (R)-4-cyano-3-hydroxybutyrate (2.04 g, 11.0 mol) in MeOH (20 ml) cooled in an ice bath, gaseous $NH_3$ was bubbled for one hour. The solution was left to stir at ambient temperature for 2 days, and during this period was insufflated 4 more times with gaseous $NH_3$ according to the same process for periods of 15 minutes at a time. At the end of this process, the solution was vacuum evaporated and the residue extracted with $Et_2O$; the solvent was removed by decanting and the residue purified by flash chromatography on silica gel using $CHCl_3$-MeOH as the eluent in a ratio of 80:20, yielding 763 mg of product as an oil (yield=54%); $_1$H NMR ($H_2O$, 200 MHz) δ 4.35 (m, 1H), 2.90–2.65 (m, 2H), 2.52 (d, 2H); $[\alpha]_D^{20}$=−11.2° (c=0.43, MeOH); C, H, N values calculated for $C_5H_8N_2O_2$: C, 46.87; H, 6.29; N, 21.85; found: C, 46.57, H, 6.02; N, 21.35.

Preparation of (R)-5-(cyanomethyl)-2-oxazolidone [5] (Step d)

To (R)-4-cyano-3-hydroxybutyramide (660 mg, 5.15 mol) in $CH_3CN$ (20 mL) and $H_2O$ (20 mL) were added pyridine (814 mg, 10.30 mol) and bis[trifluoroacetoxy]phenyl iodide (PIFA) (3.32 g, 7.725 mol), and the solution was left to stir for 6.5 hours at ambient temperature. The organic solvent was vacuum-evaporated, $H_2O$ was added (33 mL) and the solution was extracted with $Et_2O$ (3×50 mL). The volatile phase was washed with saturated NaCl solution and dried in anhydrous sodium sulphate. By evaporating the solvent, a crude product is obtained which is purified by flash chromatography on silica gel using EtOAc as the eluent until elution of a visible UV impurity, and then EtOAc-MeOH in a ratio of 9:1. 140 mg of product were obtained and 480 mg of starting product were recovered which were once again reacted in the above-described conditions. After chromatography, another 130 mg of product were obtained as an amorphous solid (270 mg total, yield=41%); melting point=68–70° C.; $^1$H NMR ($H_2O$, 200 MHz) δ 5.05 (m, 1H), 3.88 (t, 1H), 3.48 (dd, 1H), 3,03 (m, 2H); $[\alpha]_D^{20}$=+77.8° (c=1.06, $H_2O$); C, H, N values calculated for $C_5H_6N_2O_2$: C, 47.62; H, 4.79; N, 22.21; found: C, 47.31, H, 4.53; N, 22.15.

Preparation of (R)-4-amino-3-hydroxybutyric acid [6] (Step e)

A solution of (R)-5-(cyanomethyl)-2-oxazolidone (182 mg, 1.44 mol) in HCl 3N (6 mL) was heated at 100° C. for 5 days. At the end of this period, the acid water was removed by vacuum evaporation and the residue purified on Dowex 50W(H) resin, eluting first with $H_20$ up to pH=7 and then with a 5% aqueous ammonia solution. 168 mg of product were obtained (yield=97%); $^1$H NMR ($H_2O$, 200 MHz) δ 4.20 (m, 1H), 3.20 (dd, 1H), 2.95 (dd, 1H), 2.45 (d, 2H); C, H, N values calculated for $C_4H_9NO_3$: C, 40.34; H, 7.56; N, 11.76; found: C, 40.68, H, 7.62; N, 11.51. melting point: 207–209° C.; $[\alpha]_D^{20}$=−13.5° (c=1.81, $H_2O$); chiral HPLC: CROWNPAK-CR(+) column (5 μm, 150×4.6 mm), T=0° C., mobile phase=$HClO_4$ 0.042 M (3.5 ML 70% $HClO_4$ per liter of aqueous solution), flow-rate=0.5 mL/min, RI detector, retention time=9.61 min; R form (83%); S form (17%); ee 66%; (*Synthesis* 1986, 424–426) melting point=213–214° C.; $[\alpha]_D^{25}$=−20.5° (c=1.75, $H_2O$)

What is claimed is:

1. Process for the preparation of R-(−)-carnitine according to the reaction diagram:

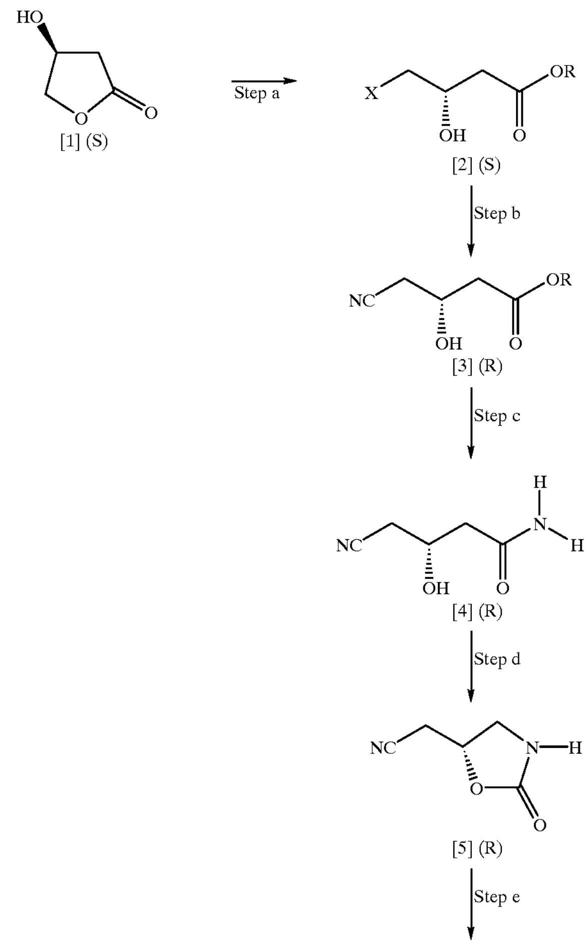

-continued

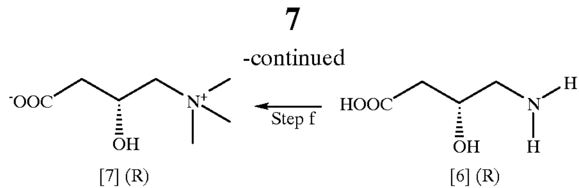

where X is halogen and R a linear or branched $C_1$–$C_7$ alkyl, comprising the following steps:

a) conversion of (S)-3-hydroxy-4-butyrolactone [1] to alkyl (S)-4-halogen-3-hydroxy-butyrate [2] by reaction with a linear or branched $C_1$–$C_7$ alcohol;

b) substitution of a CN group for the halogen of compound [2] to yield the alkyl ester of (R)-4-cyano-3-hydroxybutyric acid [3];

c) conversion of alkyl ester [3] to yield (R)-4-cyano-3-hydroxybutyramide [4];

d) cyclization of compound [4] to yield (R)-5-(cyanomethyl)-2-oxazolidone [5] via conversion of the amide function to isocyanate;

e) hydrolysis of compound [5] to yield (R)-4-amino-3-hydroxybutyric acid [6];

f) methylation of the amino group of compound [6] to yield the end product (R)-carnitine.

2. Process according to claim 1, characterized in that in step a compound [1] is esterified with an alcohol selected from the group consisting of methanol, ethanol, isopropanol and isobutanol.

3. Process according to claim 1, characterized in that in step b compound [2] is dissolved in an organic solvent selected from the group consisting of dimethylformamide, dimethylsulfoxide, acetonitrile or mixtures of these with water, and is then reacted with KCN.

4. Process according to claim 3, characterized in that the solubilization is done with solvent:water ratios ranging from 10:1 to 1:10.

5. Process according to claim 3, characterized in that a mixture of acetonitrile and $H_2O$ in ratios ranging from 2:1 to 6:1 is used as the solvent.

6. Process according to claim 1, characterized in that in step c compound [3] is dissolved in a solvent selected from the group consisting of methanol, ethanol and isopropanol and then reacted with gaseous $NH_3$.

7. Process according to claim 1, characterized in that steps b and c are carried out in sequence without purifying the product resulting from step b.

8. Process according to claim 1, characterized in that in step d compound [4] is solubilised in an organic solvent selected from the group consisting of acetonitrile, dimethylformamide, dimethylsulfoxide or mixtures of these with $H_2O$, and is then reacted with bis[trifluoro-acetoxy] phenyl iodide (PIFA), optionally in the presence of an organic base.

9. Process according to claim 8, characterized in that said solvent is a mixture of acetonitrile and $H_2O$ in ratios ranging from 1:2 to 2:1.

10. Process according to claim 8, characterized in that said organic base is selected from the group consisting of pyridine, triethylamine, trimethylamine, picoline and lutidine, and is added with a compound [4]:base ratio ranging from 1:1 to 1:3.

11. Process according to claim 1, characterized in that in step e the hydrolysis is done with an aqueous solution of a strong acid for time periods ranging from 1 hour to 7 days and at temperatures ranging from ambient temperature to the reflux temperature of the acid solution.

12. Process according to claim 11, characterized in that the strong acid is HCl at a concentration from 1N to 12N.

* * * * *